United States Patent
Lewis et al.

(10) Patent No.: US 8,277,196 B2
(45) Date of Patent: Oct. 2, 2012

(54) ADAPTIVE ACCURACY FOR ENTERAL FEEDING PUMP

(75) Inventors: Thomas G. Lewis, O'Fallon, IL (US); Jeffrey E. Price, Wildwood, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 271 days.

(21) Appl. No.: 12/813,579

(22) Filed: Jun. 11, 2010

(65) Prior Publication Data

US 2011/0305584 A1    Dec. 15, 2011

(51) Int. Cl.
F04B 49/00 (2006.01)
F04B 43/08 (2006.01)
F04B 43/12 (2006.01)
F04B 45/08 (2006.01)

(52) U.S. Cl. ............... 417/1; 417/218; 417/476
(58) Field of Classification Search .............. 417/1, 218, 417/221, 278, 279, 410.3, 412, 474, 476, 417/477.1, 477.3, 477.6, 477.7, 477.8
See application file for complete search history.

(56) References Cited

U.S. PATENT DOCUMENTS

| | | | |
|---|---|---|---|
| 2,789,514 A * | 4/1957 | Hill .......................... | 417/476 |
| 4,346,705 A | 8/1982 | Pekkarinen et al. | |
| 4,702,675 A | 10/1987 | Aldrovandi et al. | |
| 4,884,013 A | 11/1989 | Jackson et al. | |
| 5,018,945 A | 5/1991 | D'Silva | |
| 5,098,261 A | 3/1992 | Bertoncini | |
| 5,116,203 A | 5/1992 | Natwick et al. | |
| 5,318,413 A | 6/1994 | Bertoncini | |
| 5,395,320 A | 3/1995 | Padda et al. | |
| 5,486,854 A * | 1/1996 | Uchida ............................. | 347/30 |
| 5,657,000 A * | 8/1997 | Ellingboe ..................... | 340/608 |
| 7,092,797 B2 | 8/2006 | Gaines et al. | |
| 7,300,264 B2 * | 11/2007 | Souza ....................... | 417/477.11 |
| 7,462,170 B2 | 12/2008 | Fournie et al. | |
| 7,534,009 B2 | 5/2009 | Trojanowski et al. | |
| 7,608,059 B2 | 10/2009 | Harr et al. | |
| 2005/0267439 A1* | 12/2005 | Harr et al. ..................... | 604/500 |
| 2007/0068969 A1* | 3/2007 | Orzech et al. ................. | 222/214 |
| 2007/0077152 A1 | 4/2007 | Knauper et al. | |

* cited by examiner

Primary Examiner — Devon Kramer
Assistant Examiner — Bryan Lettman
(74) Attorney, Agent, or Firm — Elias Domingo (57) ABSTRACT

A pumping apparatus for use with a pump set to deliver fluid through the pump set includes a housing capable of receiving at least a portion of the pump set. A pumping device is moveably mounted in the housing and includes a motor that turns independently from movement of the pumping device when activated. The pumping device contacting the pump set when the pump set is received by the housing so the pumping device acts on the pump set to produce fluid flow in the pump set upon activation of the motor.

15 Claims, 10 Drawing Sheets

ADAPTIVE ACCURACY FOR ENTERAL FEEDING PUMP

FIELD OF INVENTION

This invention relates generally to peristaltic pumps used to deliver fluids to patients by way of a pump set, and more particularly to a peristaltic pump that compensates for conditions of the pump set.

BACKGROUND

Administering fluids containing medicine or nutrients to a patient is well known in the art. Typically, fluid is delivered to the patient by a pump set loaded on a flow control apparatus, such as a peristaltic pump, which delivers fluid to the patient at a controlled delivery rate. A peristaltic pump usually comprises a housing enclosing a rotor or the like operatively connected to at least one motor by a gearbox. The rotor drives fluid through tubing of the pump set by peristaltic action caused by rotation of the rotor driven by the motor. The motor is operatively connected to a rotatable shaft connected to the rotor, which progressively compresses the tubing and drives the fluid at a controlled rate through the pump set. The pump set may have a type of valve mechanism for permitting or preventing fluid flow through the pump set. A controller operates the motor or motors used to drive the rotor and, in some cases, controls fluid flow as by operation of the valve mechanism.

Peristaltic pumps operate by delivering fluid in small charges called "aliquots". The rotor engages the tubing of the pump set, pinching off a portion of the tubing and pushing fluid ahead of the pinch point (i.e., closer to the patient than to the source of fluid) toward the patient. Typically, the volume of fluid to be administered to the patient is controlled in the pump by counting the number of aliquots, each being of substantially the same volume, and stopping when the number corresponds to a cumulative volume of fluid desired to be delivered. Peristaltic pumps are sanitary and generally highly accurate and therefore very useful in the administration of medication and therapeutic fluids to the patient. However, the accuracy of the pump is dependent upon the dimensional stability of the tubing of the pump set. Over time the pump set tubing can be plastically (i.e., permanently) deformed so that the volume of each aliquot changes. Also, new pump sets can come in various diameters and lengths which can also affect the volume of each aliquot. Therefore, there exists a need for a compensating mechanism to account for the changes in the pump set over time as well as for dimensional variances between pump sets.

SUMMARY OF INVENTION

In one aspect of the present invention, a pumping apparatus for use with a pump set to deliver fluid through the pump set generally comprises a housing capable of receiving at least a portion of the pump set. A pumping device is moveably mounted in the housing and includes a motor that turns independently from movement of the pumping device when activated. The pumping device contacts the pump set when the pump set is received by the housing so the pumping device acts on the pump set to produce fluid flow in the pump set upon activation of the motor.

In another aspect of the present invention, a pumping apparatus for use with a pump set to deliver fluid through the pump set generally comprises a housing capable of receiving at least a portion of the pump set. A pumping device is capable of acting on the pump set to produce fluid flow within the pump set. The pumping device contacts the pump set when the pump set is received by the housing. The pumping apparatus detects a force applied to the pumping device by the pump set.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Referring now to the drawings, an enteral feeding pump (broadly, "flow control apparatus") constructed according to the principles of the present invention is generally indicated at 1. The feeding pump comprises a housing generally indicated at 3 that is constructed so as to mount a feeding set (broadly, a "pump set") generally indicated at 5 (see FIG. 6). The housing 3 includes a hinged door 7 for swinging between a closed position (FIG. 1) and an open position (FIG. 2), in which a portion of the pump 1 that receives the feeding set 5 is exposed. It will be appreciated that "housing" as used herein may include many forms of supporting structures (not shown), including without limitation multi-part structures and structures that do not enclose or house the working components of the pump 1. The pump 1 may also have a display screen generally indicated at 9 on the front of the housing 3 that is capable of displaying information about the status and operation of the pump. Buttons 11 on the side of the display screen 9 can be provided for use in controlling and obtaining information from the pump 1 and three light emitting diodes 13 can provide status information for the pump. Legs 15 at the bottom front of the housing 3 support the housing so that the display screen 9 is angled slightly upward for ease of viewing.

It should be understood that although the illustrated pump 1 is an enteral feeding pump, the present invention has application to other types of peristaltic pumps (not shown), including medical infusion pumps. The general construction and operation of the enteral feeding pump 1, except as set forth hereinafter, may be generally the same as disclosed in co-assigned U.S. Pat. No. 7,462,170 filed May 24, 2004, entitled ADMINISTRATION FEEDING SET AND VALVE MECHANISM; U.S. Pat. No. 7,608,059 filed May 24, 2004, entitled FLOW CONTROL APPARATUS; U.S. Pat. No. 7,092,797 filed May 25, 2004, entitled FLOW MONITOR- ING SYSTEM FOR A FLOW CONTROL APPARATUS; and U.S. Pat. No. 7,534,009 filed Sep. 30, 2005, entitled ALIQUOT CORRECTION FOR FEEDING SET DEGRADATION the disclosures of which are incorporated by reference. Moreover, although an exemplary feeding set 5 is shown, other types of pump sets (not shown) can be used without departing from the scope of the present invention.

Figure 3:
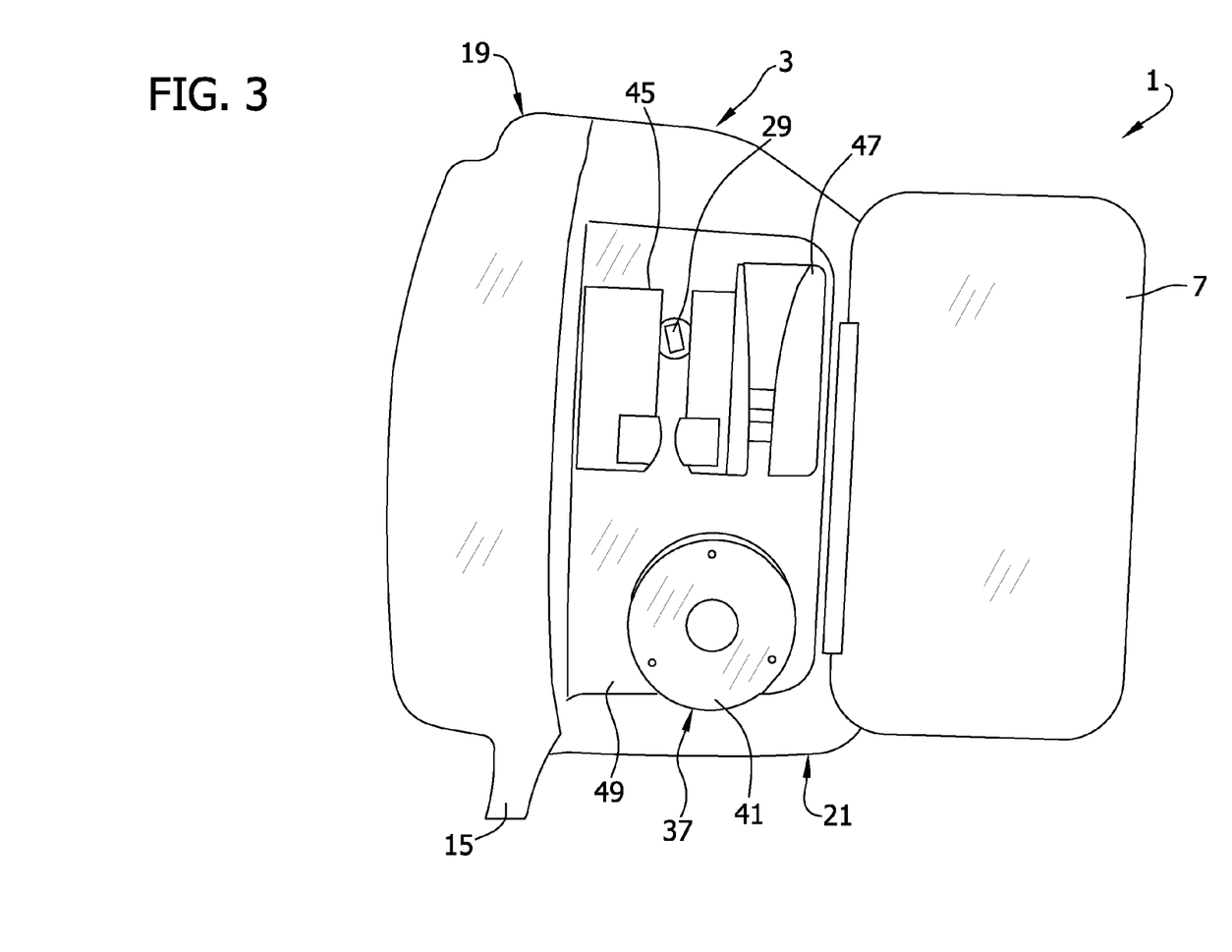
FIG. 3 is the side elevation of FIG. 2 with the feeding set removed.
Figure 4:
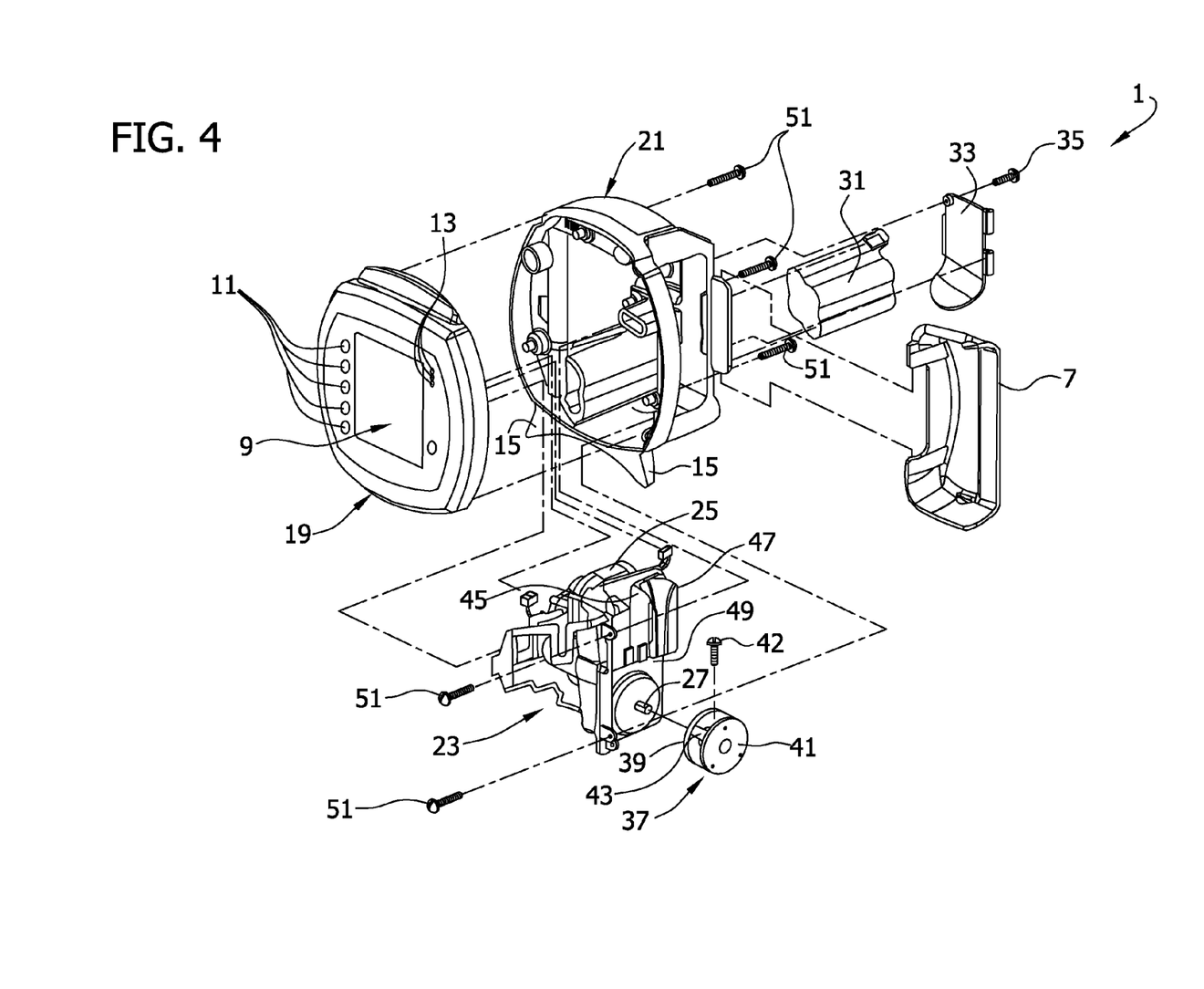
FIG. 4 is an exploded perspective of the pump.

Referring now also to FIG. 4, the display screen 9 is part of a front panel (generally indicated at 19) of the housing 3 removably attached to a main compartment (generally indicated at 21) of the housing that holds most of the operating components of the pump 1. The enteral feeding pump further includes a pumping unit (shown separated from the main compartment and indicated generally at 23) comprising a pump motor 25 connected to a rotor shaft 27 and also to a valve shaft 29 (see, FIG. 3). It will be understood that the valve shaft 29 could be omitted, and/or that a separate motor (not shown) could be provided to operate the valve shaft without departing from the scope of the present invention. A battery 31 may be received in the main compartment 21 of the housing 3 for powering the pump motor 25. A battery door 33 hingedly attached to the rear of the main compartment 21 closes the battery 31 within the compartment and provides access as needed. A fastener 35 holds the battery door 33 closed so that access to the battery 31 is normally limited. Of course, a power source other than or in addition to a battery could be used.

Figure 1:
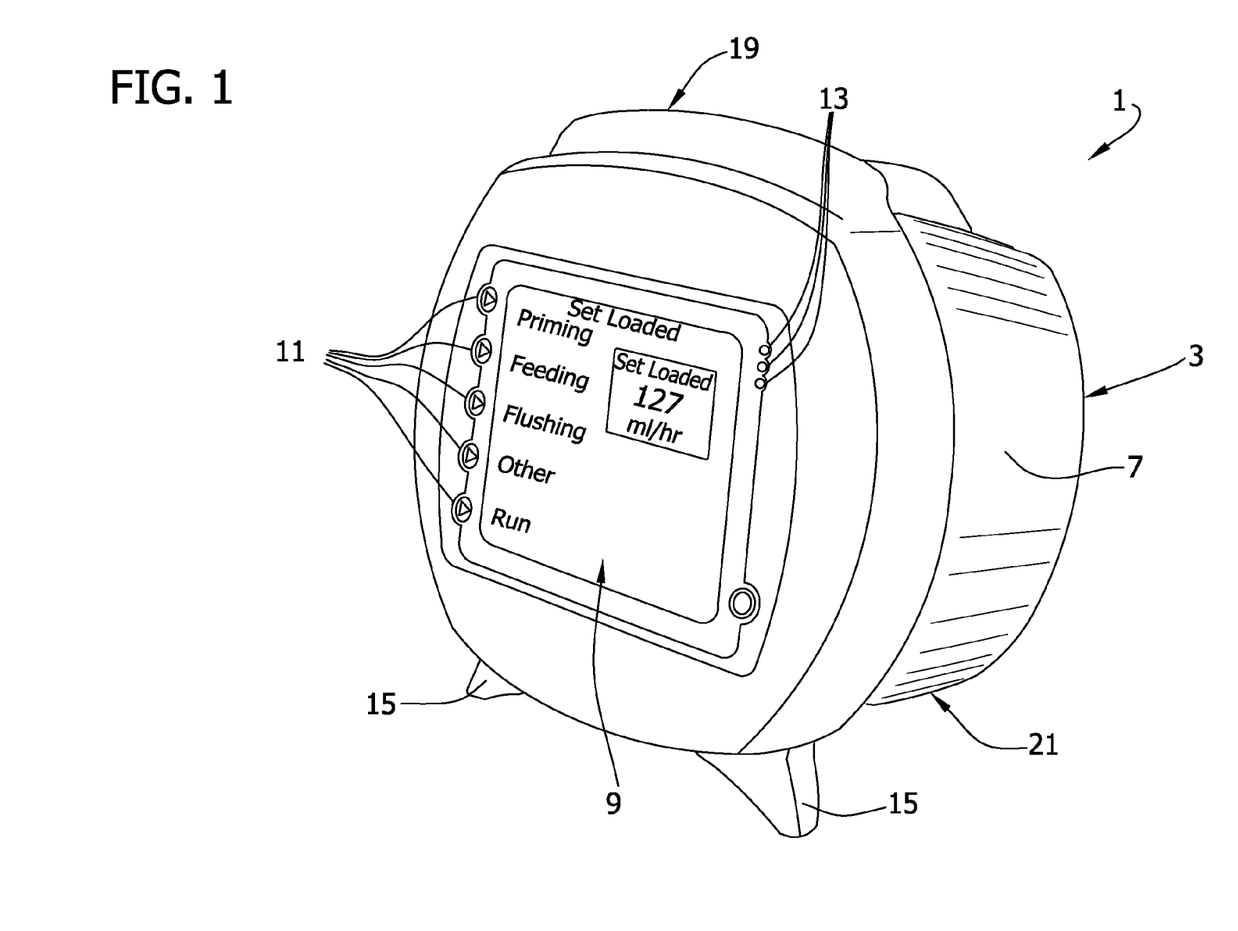
FIG. 1 is a perspective of an enteral feeding pump.

A rotor (generally indicated at 37) is mounted on the rotor shaft 27 of the pumping unit 23 by a bolt 42. The rotor 37 includes an inner disk 39, an outer disk 41, and three rollers 43 (only one of which is shown) mounted between the inner and outer disks for rotation relative to the disks about their longitudinal axes. In the illustrated embodiment, the pump motor 25, rotor shaft 27 and rotor 37 may broadly be considered "a pumping device". It should be understood that peristaltic pumps that use mechanisms other than rollers may be used without departing from the scope of the present invention. For example, a linear peristaltic pump could be used without departing from the scope of the present invention. The roller 43 engages the feeding set 5, which is also received in first and second chutes (designated 45 and 47, respectively) formed on a faceplate 49 of the pumping unit 23. The pump motor 25 is also mounted on the faceplate 49. The first and second chutes 45, 47 receive portions of the feeding set 5, as will be described in more detail hereinafter. The door 7 covers the chutes 45, 47 and rotor 37 when it is closed as shown in FIG. 1. Other fasteners 51 hold various components of the pump 1 together.

Figure 5:
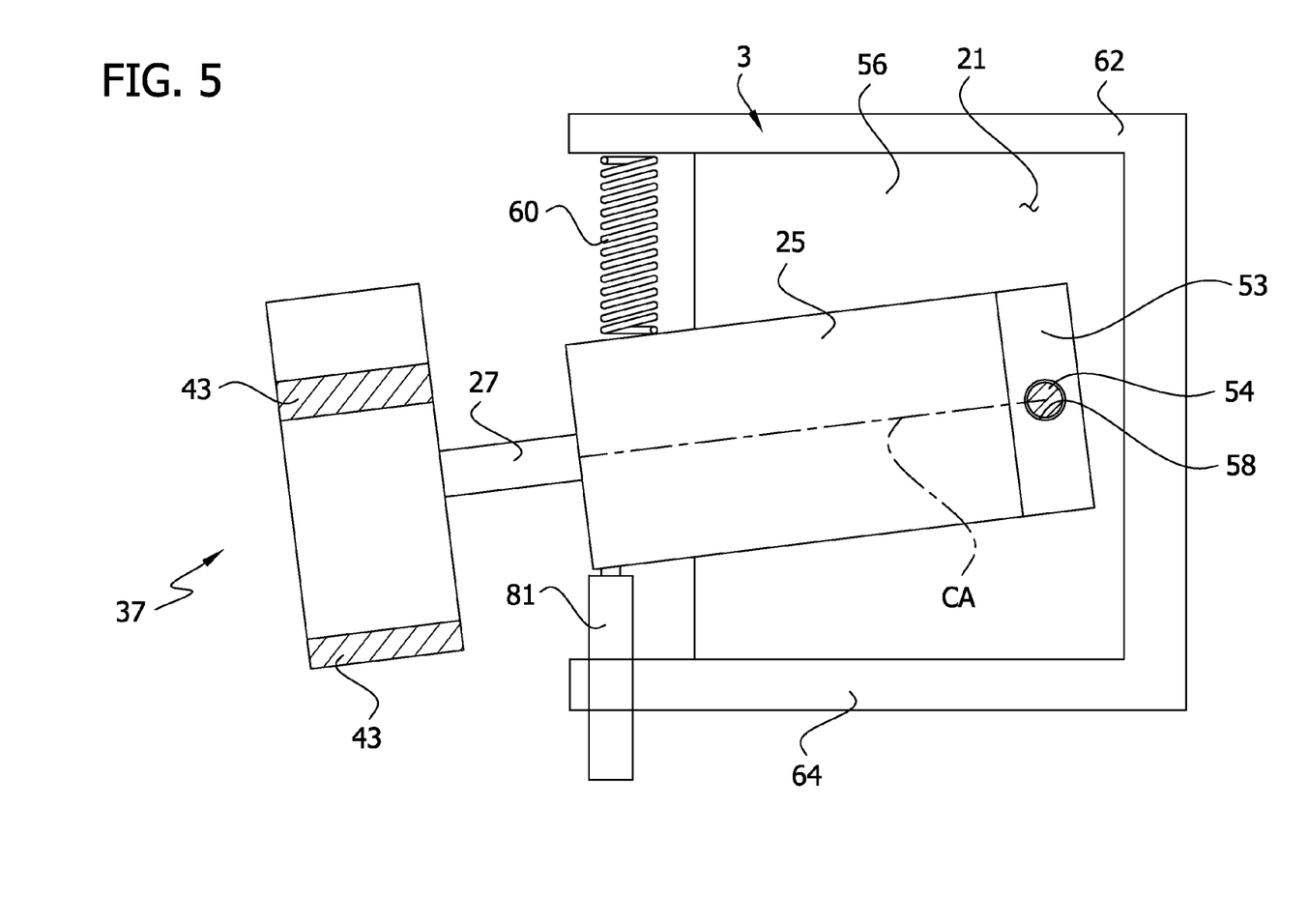
FIG. 5 is a schematic of a pumping unit and positioning sensor mounted in the pump.

Referring to FIG. 5, a mount 53 fixed to a back end of the motor 25 pivotably attaches the motor inside the main compartment 21 of the housing 3. A pivot pin 54 extends between opposite side walls 56 (only one of which is shown in FIG. 5) in the compartment 21 and through an opening 58 in the mount 53 to pivotably mount the motor 25 in the housing 3. A spring 60 attached to a top wall 62 of the compartment 21 connects to a top of the motor 25 at a front end of the motor. The spring 60 partially supports the weight of the motor 25 such that in a resting position (without the feeding set 5 mounted on the rotor 37) the motor 25 is deflected downward so a central axis CA of the motor extends about 15 degrees below horizontal. A sensor 81 is mounted is mounted to a bottom wall 64 of the compartment 21 below the motor 25 and is attached to a bottom of the motor. The sensor 81 detects the displacement of the motor 25. In one embodiment the sensor 81 is a potentiometer such as a linear potentiometer. It should be understood that other sensors such as pressure sensors for measuring the force applied to the pumping unit 23 can be used.

Figure 6:
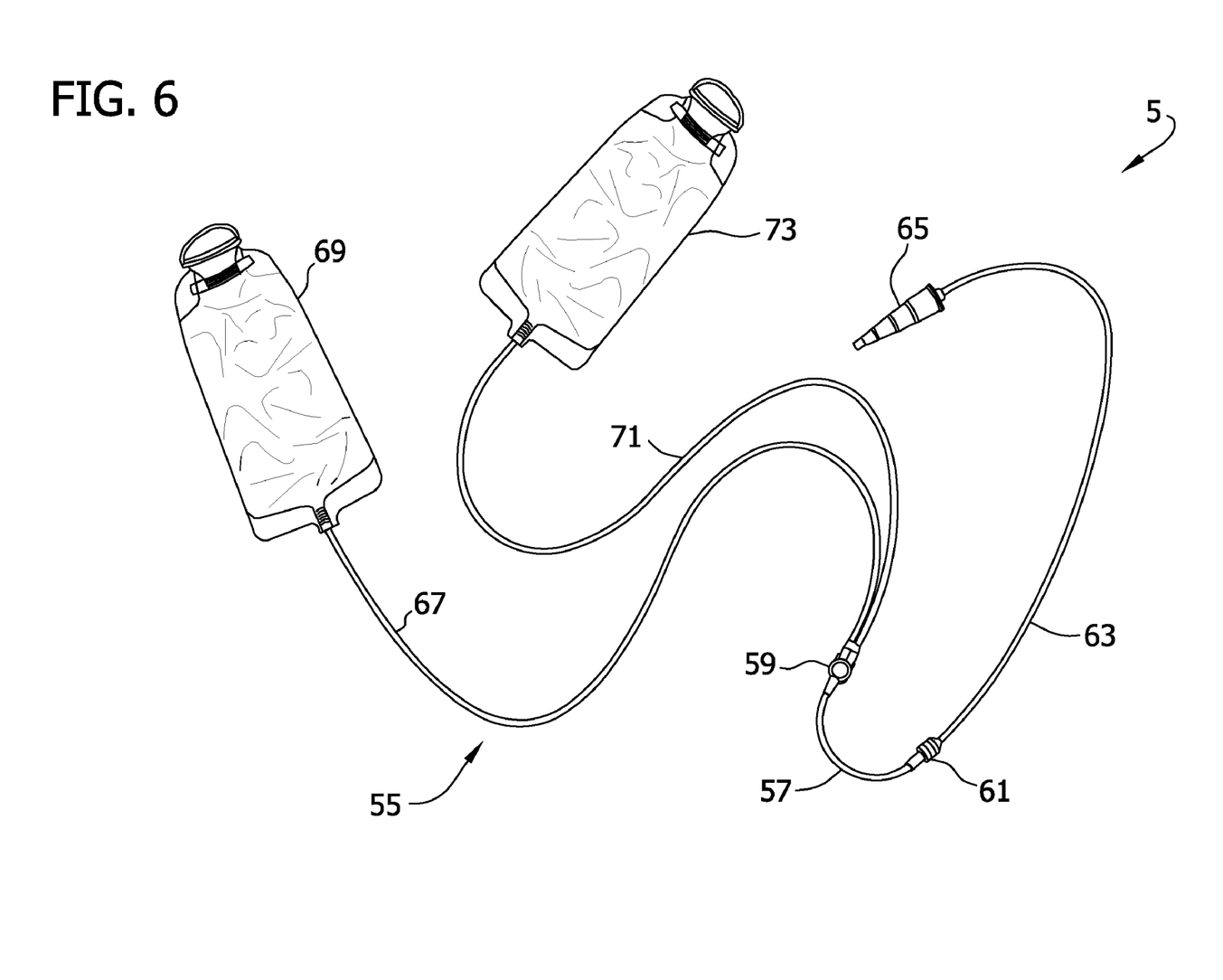
FIG. 6 is a perspective of the feeding set.

Referring now to FIG. 6, the feeding set 5 comprises tubing, indicated generally by 55, that provides a fluid pathway between at least one fluid source and a patient. In one embodiment, tubing 55 is made of a medical grade, deformable silicone and comprises a first tube section 57 connected between a valve mechanism 59 and a mounting member 61. A second tube section 63 is connected to the mounting member 61 and at an outlet of the tubing 55 to a connector, such as a barbed connector 65, suitable for connecting to a gastrostomy device (not shown) attached to a patient. A third tube section 67 is connected to an inlet of the tubing 55 to a bag 69 of feeding fluid and to valve mechanism 59, and a fourth tube section 71 is connected to an inlet of the tubing 55 of a bag 73 of flushing fluid and to the valve mechanism. The valve mechanism 59 is operable to selectively permit flow of feeding fluid from the bag 69 or flushing fluid from the bag 73, or prevent any fluid flow from the feeding or flushing fluid bags 69, 73 to the first tube section 57. The valve mechanism 59 can be turned to three positions. The first closes off all fluid flow from the third and fourth tube sections 67, 71 to the first and second tube sections 57, 63, the second allows feeding fluid to flow from the bag 69 to the first and second tube sections, and the third allows flushing fluid to flow from the bag 73 to the first and second tube sections. As previously stated, pump sets of different constructions may be used without departing from the scope of the present invention. As will be explained in greater detail below, the pump 1 is configured to adjust to the particular feeding set installed so the appropriate volume of aliquot is delivered. Examples of suitable pump sets (including valve mechanisms) are shown in co-assigned U.S. Pat. No. 7,462,170, previously incorporated by reference.

Figure 2:
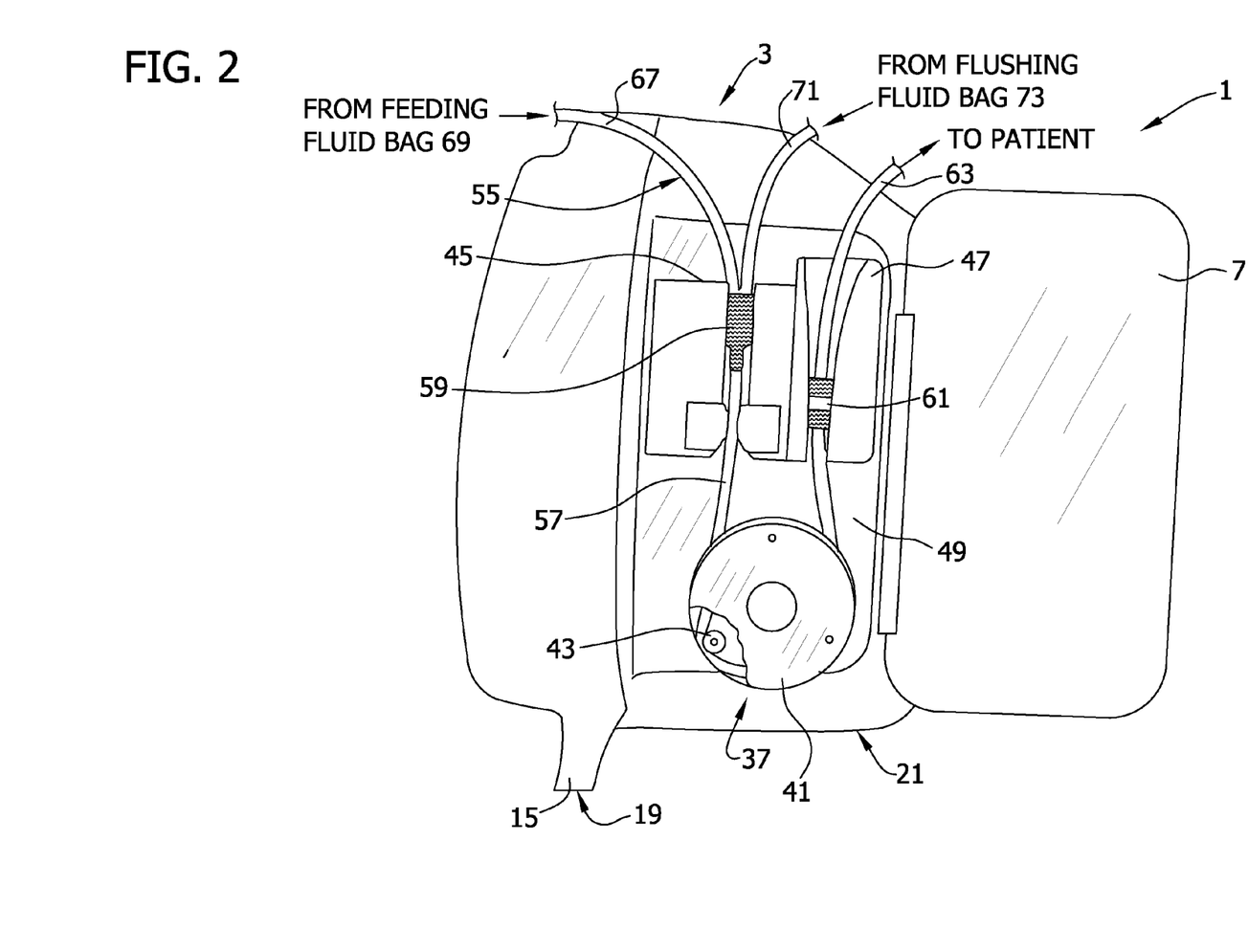
FIG. 2 is a side elevation thereof showing a fragmentary portion of a feeding set received in the pump.

In use, the feeding set feeding fluid bag 69 and flushing fluid bag 73 can be hung from a suitable support, such as an IV pole (not shown). The door 7 on the side of the pump 1 is opened and the valve mechanism 59 is placed in the first chute 45 so the valve shaft 29 of the pump is engaged with the valve mechanism (FIG. 2). Thus, rotation of the valve shaft 29 controls in which of the three positions the valve mechanism 59 is placed. The first tube section 57 is positioned around the lower part of the rotor 37 and the mounting member 61 is placed in the second chute 47. The second chute is generally funnel-shaped so the mounting member 61 can be placed in the chute 47 at a location so the first tube section 57 is substantially stretched around the rotor 37. The first tube section 57 can relax slightly, pulling the mounting member 61 farther down in the second chute 47. However, the first tube section 57 is maintained in a stretched condition around the rotor 37 when properly installed on the pump 1. The door 7 can be closed to cover the first and second chutes 45, 47 and the rotor 37. The connector 65 at the end of the second tube section 63 can be connected to a conduit (not shown) attached to the patient in a known manner. It should be understood that any suitable connector for delivering the fluid to the patient may be used without departing from the scope of the present invention.

Figure 7:
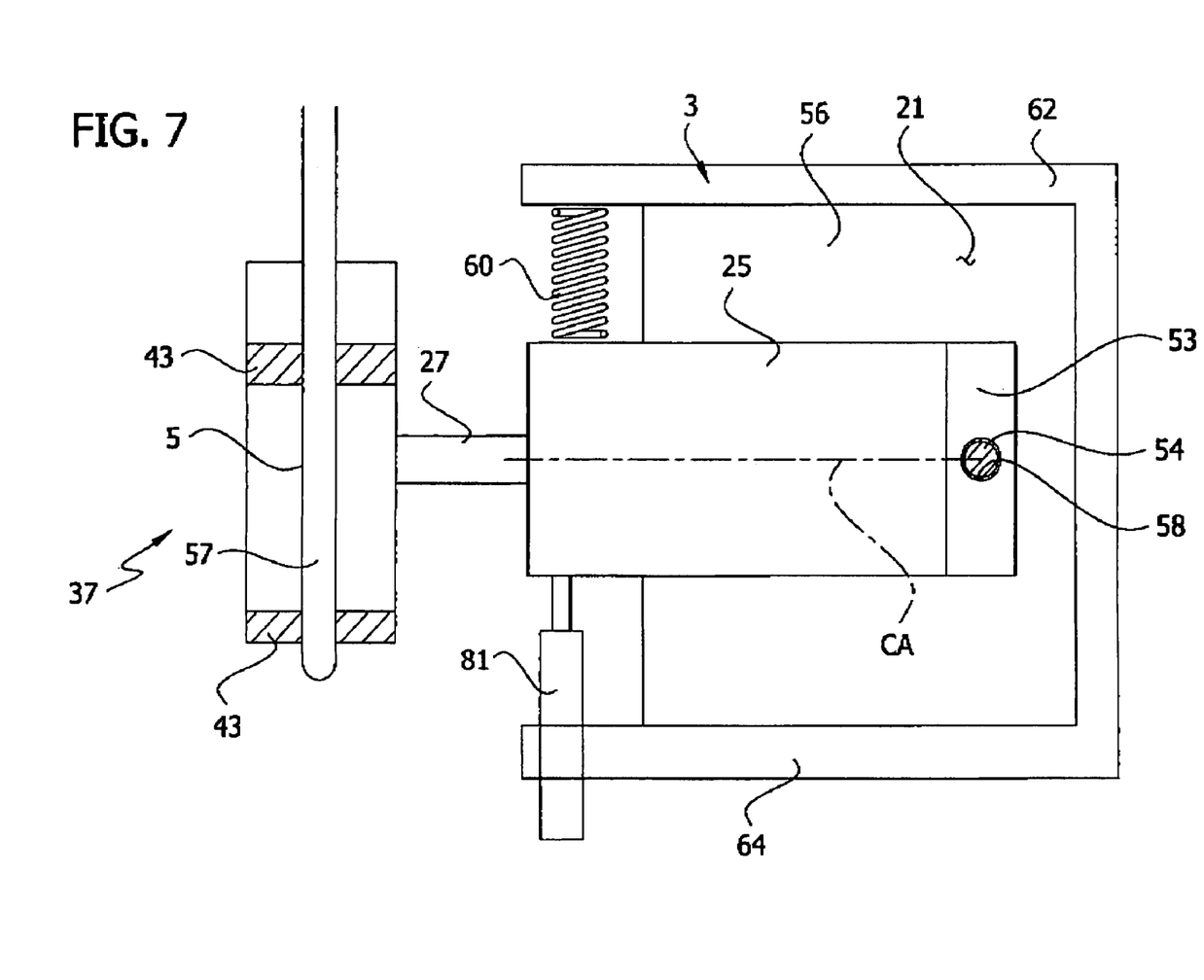
FIG. 7 is a schematic of the pumping unit and positioning sensor having the feeding set loaded on the pumping unit in a zero displacement operational condition.

In the stretched condition, the first tube section 57 causes the feeding set 5 to apply an upward force on the rotor 37. This upward force causes the motor 25 to pivot on the pivot pin 54, displacing the motor upward in proportion to the amount of the force applied by the feeding set 5 (FIG. 7). A feeding set of the customary length (e.g., about 4.75 in), when properly loaded in the pump 1, will apply about 2 lbs. of force in an upward direction, displacing the motor 25 upward about 15 degrees so that the central axis CA of the motor is substantially horizontal. The sensor 81 records a reading corresponding to the horizontal position of the motor 25. In the illustrated embodiment, the horizontal orientation represents a zero displacement operating condition. This configuration allows the pump 1 to operate optimally.

The pump 1 can be programmed or otherwise controlled to operate as desired. For instance, the pump 1 can begin operation to provide feeding fluids from the bag 69 to the patient. The care giver may select (for example) the amount of fluid to be delivered, the rate at which the fluid is to be delivered, and the frequency of fluid delivery. The pump 1 has a controller 77 (see FIG. 8) including a microprocessor 79 that allows it to accept programming and/or to include pre-programmed operational routines that can be initiated by the care giver. The controller 77 is in communication with the positioning sensor 81 detecting the amount of deflection of the feeding set 5, as previously described. Other sensors (not shown), such as a sensor that determines the type of feeding set placed in the pump 1 and/or a flow monitoring sensor can be in communication with the controller 77 to facilitate accurate pump operation. The controller 77 is also connected to the pump motor 25 for controlling its operation to actuate the valve mechanism 59 and the rotor 37. The pump motor 25 can operate the valve mechanism 59 and rotor 37 independently from each other.

Figure 8:
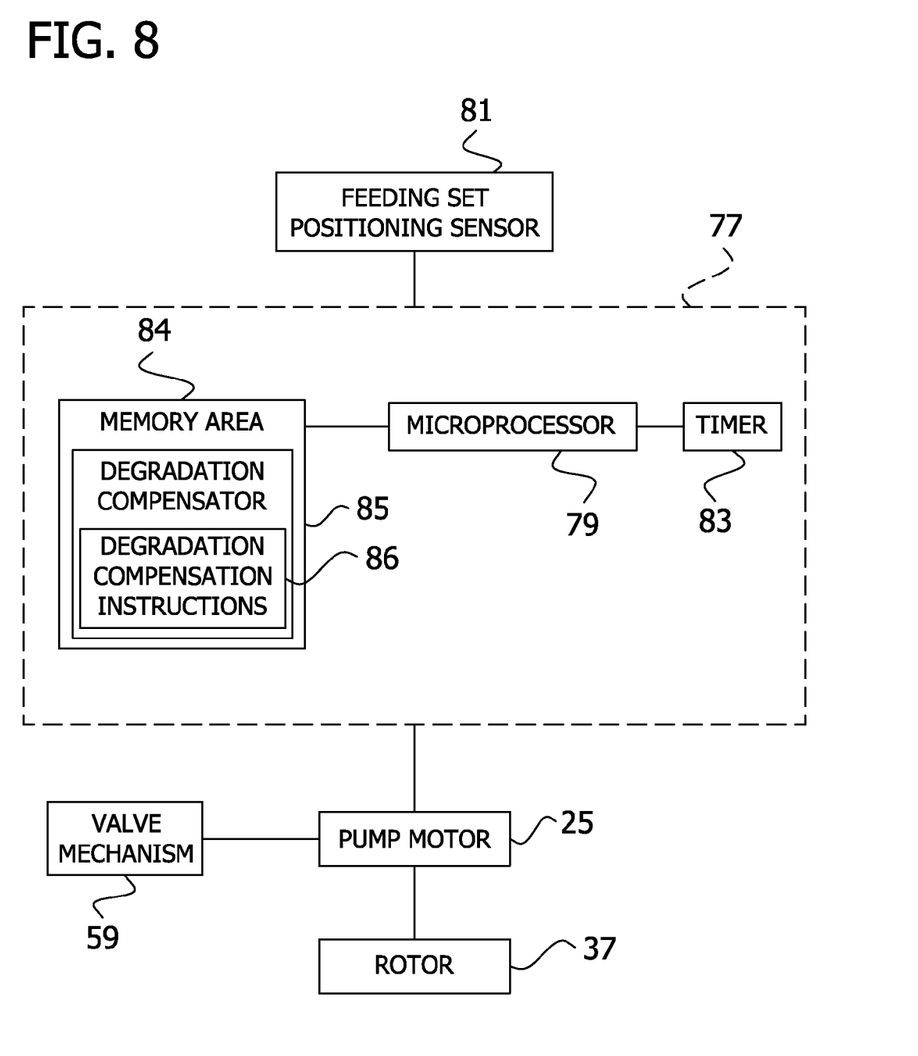
FIG. 8 is a block diagram of the components of the enteral feeding pump.

If the pump 1 is to deliver feeding fluid from the bag 69 to the patient, the valve shaft 29 is rotated so the valve mechanism 59 is moved to the second position in which fluid flows from the feeding fluid bag 69 to the first tube section 57. The amount of feeding fluid delivered to the patient is controlled by the number of rotations of the rotor 37 (in a counterclockwise direction as viewed in FIG. 2). In the illustrated embodiment, the rotor 37 includes the three rollers 43 so each third of a rotation delivers one aliquot of fluid to the patient. As each roller 43 first engages the first tube section 57, it pinches off the first tube section, closing off an amount of fluid (i.e., toward the patient) from the fluid coming from the feeding fluid bag 69. The roller 43 continues to the right, pushing fluid ahead of the roller toward the patient. Finally, the roller 43 releases engagement with the first tube section 57. As the roller releases the first tube section 57, the trailing roller engages the first tube section, pinching it off for delivering the next aliquot of fluid. Thus, when the microprocessor 79 receives a command to deliver a fluid flow rate, it calculates the number of rotations within a given period of time that will deliver a number of aliquots producing the desired flow rate. More specifically in the illustrated embodiment, the controller 77 determines the amount of time between rotations of the rotor 37. The amount of time between rotations depends upon the volume of the aliquots delivered in a single rotation. When a feeding tube of the customary length is loaded in the pump 1, the actual amount delivered to the patient is substantially the same as the amount selected by the care giver. Therefore, the controller 77 does not have to alter operation of the pump 1 to compensate for the feeding set. It should be understood that other ways of changing rotor operation could be used to maintain a constant flow rate. It has been determined that if the microprocessor programming assumes the volume of each aliquot is the same or varies only as a function of flow rate, the actual flow rate of fluid delivered. will be in error Additionally, the controller 77 of the present invention includes a timer 83 and a memory area 84 having an aliquot volume degradation compensator 85 (FIG. 8). In the illustrated embodiment, the degradation compensator 85 includes degradation compensation instructions 86. The timer 83 is initiated in a suitable manner when the feeding set 5 is first installed in the pump 1. The initiation is preferably automatic. For example, the timer 83 may initiate when the mounting member 61 is detected as being in the proper position for a certain period of time. The degradation compensator 85 operates to correct for variation in the volume associated with each aliquot of fluid delivered by the pump 1 to the patient.

The degradation compensation instructions 86 of the degradation compensator 85 are used to account for variations in aliquot volume as a result of the length and type of feeding set loaded on the pump 1. The degradation compensation instructions 86 are machine readable instructions stored on any suitable medium, broadly identified as the memory area 84. These instructions can be carried out by the microprocessor 79. The degradation compensator 85 is used to counteract the change in aliquot volume produced when feedings sets that are longer or shorter than the customary length are loaded in the pump 1. Additionally, the compensator 85 compensates for a feedings set that lengthens after a period of use.

Figure 9:
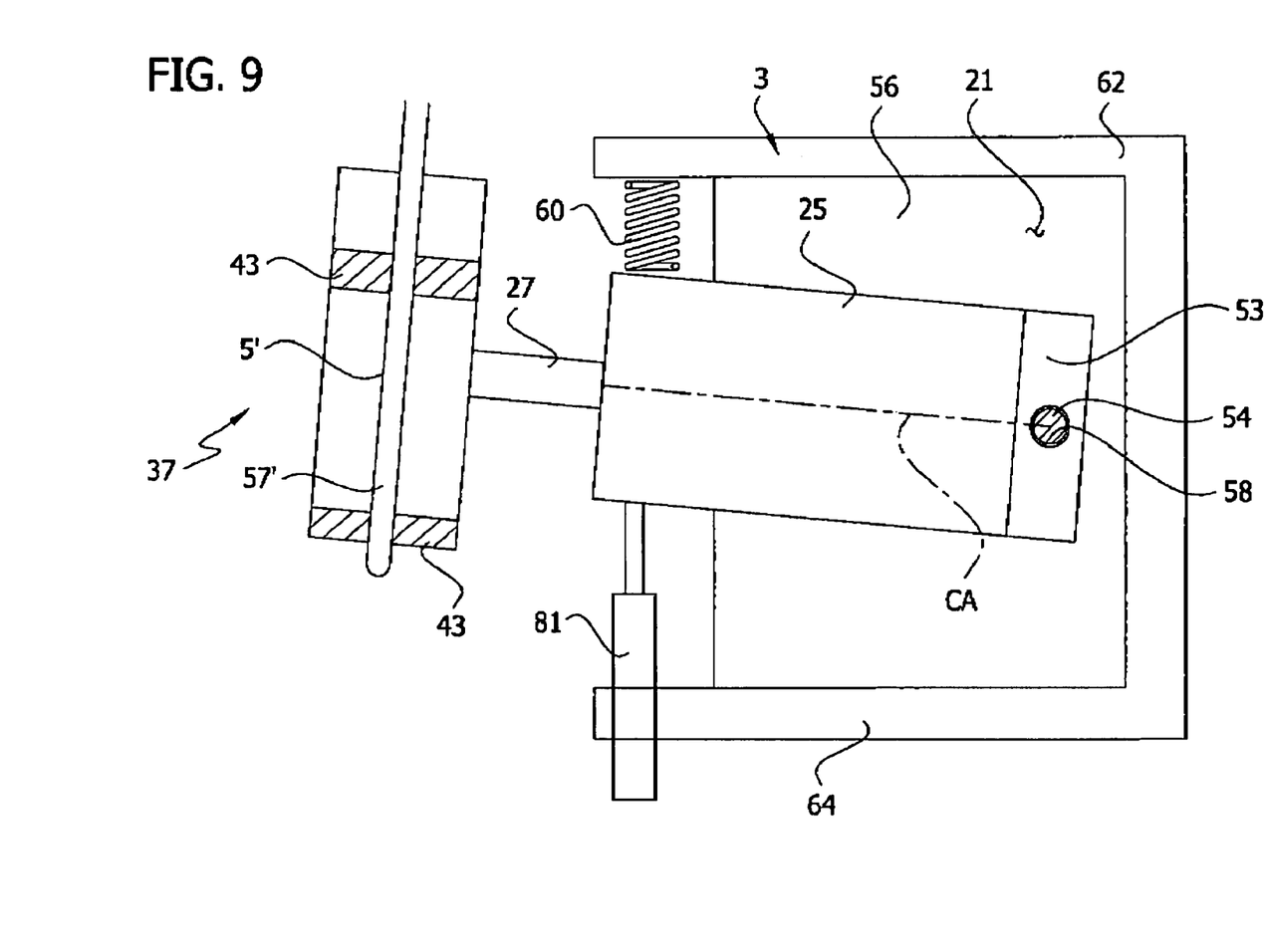
FIG. 9 is a schematic of the pumping unit and positioning sensor having the feeding set loaded on the pumping unit in a positive displacement operational condition.

In the instance where a short feeding set 5' is loaded in the pump 1, the feeding set will generate a force on the rotor 37 that is greater than the about 2 lbs of force generated by the customary length feeding set 5 discussed above. This will cause the motor 25 to pivot upward on the pivot pin 54 such that the central axis CA of the motor extends at an angle above horizontal (FIG. 9). The sensor 81 will record a reading corresponding to the position of the motor 25. In the illustrated embodiment, the above horizontal orientation represents a positive displacement operational condition. Because the feeding set 5' will be stretched to a greater degree than the "correct" length feeding set 5, the volume in the first tube section 57' of the feeding set 5' will be decreased. Thus, the aliquot volume will be less, resulting in less fluid being delivered to the patient than actually selected by the care giver. To counteract this reduction in volume, the degradation compensator 85 processes the reading from the sensor 81 and determines that the pump 1 is operating in a positive displacement operational condition. The degradation compensation instructions 86 then signal to the motor 25 to increase the rate of delivery of the fluid to compensate for the smaller volume aliquots (i.e., increase number of rotations of the rotor 37). Therefore, in a given amount of time, the pump 1 will deliver the same amount of fluid to the patient as would have been delivered with a feeding set of the customary length.

Figure 10:
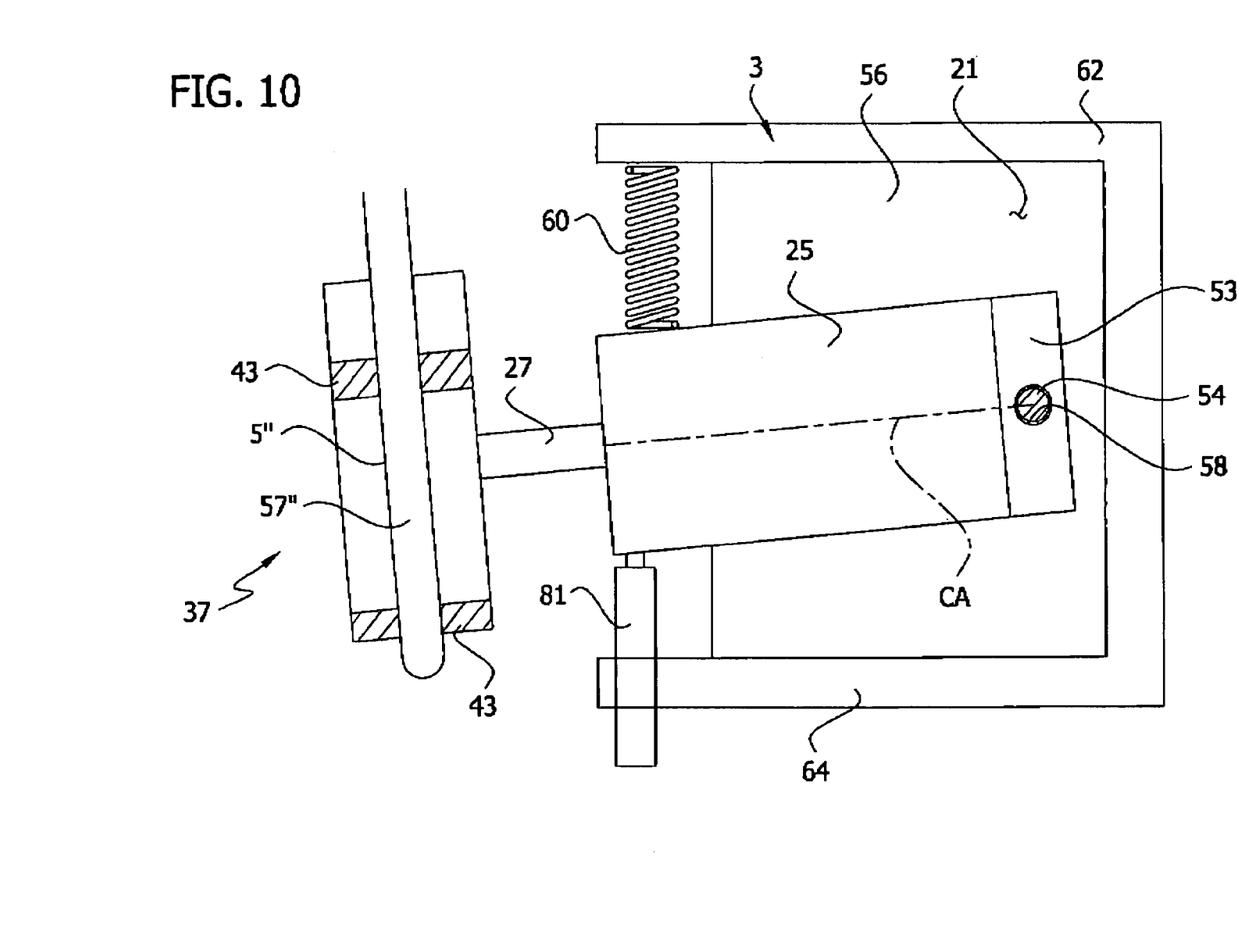
FIG. 10 is a schematic of the pumping unit and positioning sensor having the feeding set loaded on the pumping unit in a negative displacement operational condition.

Conversely, if a long feeding set 5" is loaded in the pump 1, the feeding set will generate a force on the rotor 37 that is less than the about 2 lbs. of force generated by the customary length feeding set 5 discussed above. This will cause the motor 25 to pivot downward on the pivot pin 54 such that the central axis CA of the motor extends at an angle below horizontal (FIG. 10). The sensor 81 will record a reading corresponding to the position of the motor 25. In the illustrated embodiment, the below horizontal orientation represents a negative displacement operational condition. Because the feeding set 5" will be stretched to a lesser degree than the customary length feeding set 5, the volume in the first tube section 57' of the feeding set 5" will be increased. Thus, the aliquot volume will be greater, resulting in more fluid being delivered to the patient than actually selected by the care giver. To counteract this increase in volume, the degradation compensator 85 processes the reading from the sensor 81 and determines that the pump 1 is operating in a negative displacement operational condition. The degradation compensation instructions 86 then signal to the motor 25 to decrease the rate of delivery of the fluid to compensate for the larger volume aliquots (i.e., decrease number of rotations of the rotor 37). Therefore, in a given amount of time, the pump 1 will deliver the same amount of fluid to the patient as would have been delivered with a feeding set of the customary length. It will be understood that the pump 1 can perform the same compensation process for a customary length feeding tube that has been stretched over time. The sensor 81 can record a reading of the motor displacement prior to operation of the motor 25 and during operation to provide a continuous monitoring of the fluid delivery. Also, the pump 1 and motor 25 could be configured to operate in an optimal condition in a position other than substantially horizontal. Although a pivot connection for pivoting movement is shown in the illustrated embodiment, the motor 25 could be configured to move in other ways, such as by substantially linear movement or a combination of rotational and linear movement.

As a safety measure, the aliquot correction mechanism of the present invention can be used as a limit for feeding sets that exceed minimum and maximum allowable lengths. In this case, deflection by the motor 25 above or below the horizontal beyond a predetermined degree will result in the controller 77 instructing the pump 1 that it is in a "no pump" configuration. If a pressure sensor is used, forces above or below predetermined values will indicate to the controller 77 that the feeding set is not within the allowable length range. Further, the mechanism can function as an indicator for determining whether the feeding set has been installed on the pump. In this instance, movement of the motor 25 from its resting position shown in FIG. 5 will signal to the controller 77 that a feeding set has been loaded in the pump 1. A feeding set having a length that is unable to move the motor 25 from its resting position will not be sufficient to signal to the controller that a feeding set has been properly loaded. A feeding set having this length will also signal to the controller that it exceeds the maximum allowable length. Embodiments using a pressure sensor can also be used to indicate whether a feeding set has been loaded in the pump 1. Here, a pressure change from the state of the pump 1 in FIG. 5 will signal to the controller 77 that a feeding set has been loaded. If no pressure change occurs, then the pump 1 will indicate that a feeding set has not been loaded or alternatively, that the feeding set exceeds the maximum allowable length.

Thus it may be seen that the various objects and features of the present invention are achieved by the embodiment of the pump 1 disclosed herein. The pump controller 77 has the degradation compensator 85 allowing the microprocessor 79 to compensate for changes in aliquot volume of the pump 1 based on the displacement of the motor 25 by the feeding set 5. The pump 1 is able to allow for the degradation (or changes) in the dimensions of the feeding set 5 both over time and by changing the feeding set. Therefore, the patient can receive accurate flow rates of fluid regardless of the feeding set.

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, microprocessor 79 of the controller 77 executes computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage media including memory storage devices.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements. Moreover, the use of "up", "down", "top", and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A pumping apparatus for use with a pump set to deliver a fluid through the pump set, the pumping apparatus comprising:
a housing capable of receiving at least a portion of the pump set; and
a pumping device pivotally mounted in the housing and comprising a motor that rotates a pump rotor independent from a pivoting movement thereof relative to the housing, the pump rotor contacting the pump set when the pump set is received by housing such that the pump rotor rotates to repeatedly contact the pump set to produce a fluid flow through the pump set upon rotation of the motor and pump rotor.

2. The pumping apparatus of claim 1 wherein the the pivoting movement of the pumping device depends upon physical characteristics of the pump set.

3. The pumping apparatus of claim 1 further comprising a spring biasing the motor in an upward direction.

4. The pumping apparatus of claim 3 further comprising a pivot pin pivotably connected to the housing, the spring and pivot pin supporting the pumping device in the housing.

5. The pumping apparatus of claim 3 further comprising a sensor operatively connected between the pumping device and the housing, the sensor sensing the pivoting movement of the pumping device.

6. The pumping apparatus of claim 5 wherein the sensor comprises a linear potentiometer.

7. The pumping apparatus of claim 5 further comprising a controller programmed to control an operation of the pumping device, the controller altering the operation of the pumping device in response to the pivoting movement sensed by the sensor.

8. The pumping apparatus of claim 2 wherein the pumping device moves to a substantially horizontal orientation relative to a top and bottom of the housing contacting a pump set having a first length, and wherein the pumping device moves to an orientation above horizontal when contacting a pump set having a second length shorter than the first length, and wherein the pumping device moves to an orientation below horizontal when contacting a pump set having a third length longer than the first length.

9. The pumping apparatus of claim 2 further comprising a controller programmed to control an operation of the pumping device, the controller sensing when the pump rotor contacts the pump set.

10. A pumping apparatus for use with a pump set to deliver a fluid through the pump set, the pumping apparatus comprising:
   a housing capable of receiving at least a portion of the pump set; and
   a pumping device pivotally mounted in the housing and comprising a motor that rotates a pump rotor independent of a pivoting movement thereof relative to the housing, the pump rotor acting on the pump set to produce a fluid flow through the pump set, the pump rotor contacting the pump set when the pump set is received by the housing; and wherein the pumping apparatus detects a force applied to the pumping device by the pump set.

11. The pumping apparatus of claim 10 wherein the pumping apparatus detects a force applied to the motor of the pumping device.

12. The pumping apparatus of claim 11 further comprising a sensor operatively connected between the pumping device and the housing, the sensor sensing said force applied to the pumping device.

13. The pumping apparatus of claim 12 wherein the sensor is a pressure sensor.

14. The pumping apparatus of claim 12 further comprising a controller programmed to control an operation of the pumping device, the controller altering the operation of the pumping device in response to the force sensed by the sensor.

15. The pumping apparatus of claim 10 further comprising a controller programmed to control an operation of the pumping device, the controller sensing when the pumping apparatus engages the pump set.

\* \* \* \* \*

UNITED STATES PATENT AND TRADEMARK OFFICE
CERTIFICATE OF CORRECTION

PATENT NO. : 8,277,196 B2  Page 1 of 1
APPLICATION NO. : 12/813579
DATED : October 2, 2012
INVENTOR(S) : Thomas G. Lewis et al.

It is certified that error appears in the above-identified patent and that said Letters Patent is hereby corrected as shown below:

In col. 6, line 56, change "section 57' of the feeding set" to --section 57" of the feeding set--.

Signed and Sealed this
Nineteenth Day of March, 2013

Teresa Stanek Rea
*Acting Director of the United States Patent and Trademark Office*